US011278748B2

(12) United States Patent
Hashimoto et al.

(10) Patent No.: US 11,278,748 B2
(45) Date of Patent: Mar. 22, 2022

(54) ENDOTHELIN-CONVERTING ENZYME INHIBITOR

(71) Applicants: KAO CORPORATION, Tokyo (JP); CHULALONGKORN UNIVERSITY, Pathumwan (TH)

(72) Inventors: Hiroshi Hashimoto, Edogawa-ku (JP); Mitsuyuki Hotta, Sakura (JP); Ongpipattanakul Boonsri, Bangkok (TH); Suttisri Rutt, Bangkok (TH); Petchprayoon Chutima, Bangkok (TH); Thitikornpong Woratuch, Bangkok (TH)

(73) Assignees: KAO CORPORATION, Tokyo (JP); CHULALONGKORN UNIVERSITY, Pathumwan (TH)

( * ) Notice: Subject to any disclaimer, the term of this patent is extended or adjusted under 35 U.S.C. 154(b) by 0 days.

(21) Appl. No.: 16/348,095

(22) PCT Filed: Oct. 31, 2017

(86) PCT No.: PCT/JP2017/039319
§ 371 (c)(1),
(2) Date: May 7, 2019

(87) PCT Pub. No.: WO2018/088272
PCT Pub. Date: May 17, 2018

(65) Prior Publication Data
US 2019/0299033 A1    Oct. 3, 2019

(30) Foreign Application Priority Data
Nov. 9, 2016 (WO) .................. PCT/JP2016/083181

(51) Int. Cl.
| A61K 8/97 | (2017.01) |
| A61Q 19/02 | (2006.01) |
| A61K 8/9794 | (2017.01) |
| A61K 8/9789 | (2017.01) |
| A61P 17/18 | (2006.01) |
| A61K 36/48 | (2006.01) |
| A61K 36/67 | (2006.01) |
| A61K 36/81 | (2006.01) |
| A61K 36/899 | (2006.01) |
| A61K 36/90 | (2006.01) |
| A61K 36/185 | (2006.01) |
| A61P 9/12 | (2006.01) |

(52) U.S. Cl.
CPC ............ *A61Q 19/02* (2013.01); *A61K 8/9789* (2017.08); *A61K 8/9794* (2017.08); *A61K 36/185* (2013.01); *A61K 36/48* (2013.01); *A61K 36/67* (2013.01); *A61K 36/81* (2013.01); *A61K 36/899* (2013.01); *A61K 36/90* (2013.01); *A61P 9/12* (2018.01); *A61P 17/18* (2018.01)

(58) Field of Classification Search
None
See application file for complete search history.

(56) References Cited

U.S. PATENT DOCUMENTS

| 2004/0028756 A1* | 2/2004 | Teather .................. A61K 31/55 424/752 |
| 2005/0191267 A1* | 9/2005 | Luanratana .......... A61K 36/488 424/74 |

FOREIGN PATENT DOCUMENTS

JP    3441395 B2    9/2003

OTHER PUBLICATIONS

Serrano et al. Anxiolytic-like effects of erythrinian alkaloids from Erythrina Suberosa. Quim. Nova, vol. 34, No. 5, 808-811. (Year: 2011).*
International Search Report and Written Opinion dated Apr. 3, 2018 in PCT/JP2017/039319 filed on Oct. 31, 2017.
Gilchrest, B. A. et al., "Mechanisms of Ultraviolet Light-Induced Pigmentation," Photochemistry and Photobiology, 1996, vol. 63, No. 1, pp. 1-10.
Imokawa, G. et al., "Endothelins Secreted from Human Keratinocytes Are Intrinsic Mitogens for Human Melanocytes," The Journal of Biological Chemistry, 1992, vol. 267, No. 34, pp. 24675-24680.
Imokawa, G. et al., "Endothelin-1 as a New Melanogen: Coordinated Expression of Its Gene and the Tyrosinase Gene in UVB-Exposed Human Epidermis," The Journal of Investigative Dermatology, 1995, vol. 105, No. 1, pp. 32-37.
Hachiya, A. et al., "The Inhibitory Effect of an Extract of *Sanguisorba officinalis* L. on Ultraviolet B-Induced Pigmentation via the Suppression of Endothelin-Converting Enzyme-1α," Biol. Pharm. Bull., 2001, vol. 24, No. 6, pp. 688-692, XP055385109.
Kobayashi, A. et al., "Inhibitory Mechanism of an Extract of *Althaea officinalis* L. on Endothelin-1-Induced Melanocyte Activation," Biol. Pharm. Bull., 2002, vol. 25, No. 2, pp. 229-234, XP055385112.
Temkitthawon, P. et al., "Screening for phosphodiesterase inhibitory activity of Thai medicinal plants," Journal of Ethnopharmacology, 2008, vol. 119, pp. 214-217, XP025399338.
Yadav, S. et al., "Production, Isolation and Identification of Flavonoids From Aerial Parts of Hiptage Benghalensis," Life Science, 2012, vol. 2, No. 3, pp. 1-5, XP055385561.

(Continued)

*Primary Examiner* — Jessica Worsham
(74) *Attorney, Agent, or Firm* — Oblon, McClelland, Maier & Neustadt, L.L.P.

(57) ABSTRACT

Provision of a material, which has activity of inhibiting endothelin-converting enzyme and is effective for skin whitening or antihypertension. An endothelin-converting enzyme inhibitor comprising, as an active ingredient, at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

6 Claims, No Drawings

(56) References Cited

OTHER PUBLICATIONS

Romero, M. et al., "Quercetin inhibits vascular superoxide production induced by endothelin-1: Role of NADPH oxidase, uncoupled eNOS and PKC," Atherosclerosis, 2009, vol. 202, pp. 58-67, XP026119706.
Choi, M-H. et al., "Anti-Melanogenesis Effect of Quercetin," cosmetics, 2016, vol. 3, pp. 1-16, XP055385568.
Anonymous, "HIPTAGE Gaertner, Fruct. Sem. Pl. 2: 169. 1790, nom. cons.," Fl. China 11, 2008, pp. 135-138, 5 total pages, XP055385678.

* cited by examiner

ENDOTHELIN-CONVERTING ENZYME INHIBITOR

FIELD OF THE INVENTION

The present invention relates to a material having activity of inhibiting endothelin-converting enzyme.

BACKGROUND OF THE INVENTION

Endothelin (ET) is a bioactive factor, which continuously contracts vascular and non-vascular smooth muscles via direct and indirect actions. An increase in the action of endothelin is considered to provide a continuous vasoconstriction to blood vessels in peripheral sites, kidney and brain, and is considered to cause various diseases such as hypertension, myocardial infarction, stroke, acute renal failure, Raynaud's syndrome, atherosclerosis, asthma and prostate cancer. Three types of endothelin family peptides (ET-1, ET-2, and ET-3) having similar structures to one another are present in animals including humans, and all of these peptides have vasoconstriction action and vasopressor action.

In recent years, the role of endothelin in various cells other than vascular smooth muscle cells has been elucidated. For example, it has been reported in Non-Patent Documents 1-3 that generation of ET-1 and other factors is increased in keratinocytes when the skin is exposed to UV irradiation, and that ET-1 is suggested to be associated with melanogenesis in melanocytes exposed to UV irradiation. Accordingly, suppression of the expression of endothelin is considered to be useful, not only for prevention and/or treatment of the aforementioned various diseases, but also for prevention or amelioration of skin pigmentation.

Endothelin is a peptide consisting of 21 amino acid residues. In the biosynthetic process of endothelin, a prepropeptide is generated from mRNA, and it is then processed into an intermediate (wherein the intermediates of ET-1, ET-2, and ET-3 are referred to as Big ET-1, Big ET-2, and Big ET-3, respectively). Thereafter, such an intermediate is converted to a mature endothelin consisting of 21 amino acid residues. The intermediate has almost no vasoconstriction action, whereas the mature endothelin has strong vasoconstriction action. The enzyme, which converts the intermediate to the mature endothelin, is endothelin-converting enzyme (ECE). Conventionally, it has been reported that examples of a plant material having ECE inhibitory activity include extracts obtained from burnet (*Sanguisorba officinalis*), hawthorn (*Crataegus laevigata*), clove (*Syzygium aromaticum*), rose fruit (fruit of Rosa multiflora), gambir (*Uncaria gambir*), linden (*Tilia miqueliana*), licorice (*Glycyrrhiza glabra*), mulberry bark (*Morus alba*), rosemary (*Rosmarinus officinalis*), Assam tea plant (*Camellia sinensis* var. *assamica*), Japanese white birch (*Betula platyphylla* var. *japonica*), tormentilla (*Potentilla tormentilla*), thyme (*Thymus*), gentian (*Gentiana lutea*), geranium (*Geranium nepalense*), ginseng (*Panax ginseng* C. A. Mayer), cinchona (*Cinchona succirubra*), Japanese green gentian (*Swertia japonica*), centella (*Centella asiatica*), capillary artemisia (*Artemisia capillaris*), rehmannia root (*Rehmannia glutinosa*), honeysuckle (*Lonicera japonica*), and peppermint (*Mentha piperita*) (Non-Patent Document 4, and Patent Document 1).

(Patent Document 1) Japanese Patent No. 3441395
(Non-Patent Document 1) Photochem. Photobiol., 63, 1-10 (1996)
(Non-Patent Document 2) J. Biol. Chem., 267, 24675-24680 (1992)
(Non-Patent Document 3) J. Invest. Dermatol., 105, 32-37 (1995)
(Non-Patent Document 4) Biol. Pharm. Bull. 24, 688-692 (2001)

SUMMARY OF THE INVENTION

The present invention provides an endothelin-converting enzyme inhibitor, comprising, as an active ingredient, at least one selected from the group consisting of *Hiptage candicans*, *Piper sarmentosum*, *Solanum stramonifolium*, *Anaxagorea luzonensis*, *Smilax corbularia*, *Ardisia elliptica*, *Erythrina suberosa*, *Dactyloctenium aegyptium*, *Hopea ferrea* and extracts thereof.

The present invention provides a melanogenesis inhibitor, comprising, as an active ingredient, at least one selected from the group consisting of *Hiptage candicans*, *Piper sarmentosum*, *Solanum stramonifolium*, *Anaxagorea luzonensis*, *Smilax corbularia*, *Ardisia elliptica*, *Erythrina suberosa*, *Dactyloctenium aegyptium*, *Hopea ferrea* and extracts thereof.

Moreover, the present invention provides a skin whitening agent, comprising, as an active ingredient, at least one selected from the group consisting of *Hiptage candicans*, *Piper sarmentosum*, *Solanum stramonifolium*, *Anaxagorea luzonensis*, *Smilax corbularia*, *Ardisia elliptica*, *Erythrina suberosa*, *Dactyloctenium aegyptium*, *Hopea ferrea* and extracts thereof.

Furthermore, the present invention provides an antihypertensive agent, comprising, as an active ingredient, at least one selected from the group consisting of *Hiptage candicans*, *Solanum stramonifolium*, *Anaxagorea luzonensis*, *Smilax corbularia*, *Ardisia elliptica*, *Erythrina suberosa*, *Dactyloctenium aegyptium*, *Hopea ferrea* and extracts thereof.

DETAILED DESCRIPTION OF THE INVENTION

All patent documents, non-patent documents, and other publications cited in the present description are incorporated herein by reference in their entirety.

The present invention relates to provide a material, which has activity of inhibiting endothelin-converting enzyme and is effective for skin whitening or antihypertension.

As a result of intensive studies, the present inventors have discovered a group of plants having activity of inhibiting endothelin-converting enzyme.

The present invention provides a plant-derived material having endothelin-converting enzyme inhibiting activity. Such a material is effective for inhibition of melanogenesis in skin melanocytes, skin whitening, or prevention or amelioration of symptoms or conditions caused by an increase in endothelin activity, such as hypertension.

In the present description, the "endothelin (ET)" includes three types of endothelin subtypes, namely, ET-1 (endothelin-1), ET-2 (endothelin-2), and ET-3 (endothelin-3). In a preferred embodiment, the endothelin (ET) in the present description indicates ET-1.

In the present description, the "endothelin-converting enzyme (ECE)" includes enzyme which converts Big ET-1 to ET-1 (endothelin-converting enzyme 1; ECE-1), enzyme which converts Big ET-2 to ET-2 (endothelin-converting enzyme 2; ECE-2), and enzyme which converts Big ET-3 to ET-3 (endothelin-converting enzyme 3; ECE-3). In a preferred embodiment, the endothelin-converting enzyme in the present description indicates endothelin-converting enzyme 1 (ECE-1).

The term "non-therapeutic" is used in the present description to include a concept, which does not include medical treatments, namely, a concept, which does not include a method for performing an operation on, treating or diagnosing a human, and more specifically, a concept, which does not include a method by which a doctor or a person who has received instructions from the doctor performs an operation on, treats, or diagnoses a human.

The term "prevention" as used in the present description means prevention, suppression or delay of the onset of symptom or condition in individual bodies, or reduction in the risk of the onset of symptom or condition in individual bodies. The term "amelioration" as used in the present description means an improvement in symptom or condition, prevention, suppression or delay of aggravation of symptom or condition, or reverse, prevention, suppression or delay of the progress of symptom or condition.

The term "plant used in the present invention" as used in the present description means any one or more plants selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium*, and *Hopea ferrea*.

*Hiptage candicans* is a plant belonging to the family Malpighiaceae, and is usually used as a tonic or blood tonic.

*Piper sarmentosum* is a climber belonging to the family Piperaceae, and is conventionally applied as an expectorant, carminative or appetite stimulant, and its leaves are also used as food. In addition, *Piper sarmentosum* has been known to have antihypertensive action (Clinica Terapeutica Volume 164, Issue 6, 2013, Pages 529-535).

*Solanum stramonifolium* is a plant belonging to the family Solanaceae. Its roots are traditionally employed as an antipyretic, an analgesic, or an expectorant.

*Anaxagorea luzonensis* is a plant belonging to the family Annonaceae. The stem of this plant is traditionally used for its tonic, analgesic, antipyretic or anti-inflammatory effects.

*Smilax corbularia* is a climber belonging to the family Smilacaceae. Its rhizome is traditionally applied in the treatment of inflammation, skin diseases, bacterial infection, or sexually transmitted diseases.

*Ardisia elliptica* is a plant belonging to the family Myrsinaceae. Its roots are used in the treatment of snake bite or sexually transmitted diseases, whereas its stem is traditionally used as a treatment for leprosy or skin disease.

*Erythrina suberosa* is a tree belonging to the family Leguminosae. The leaves of this plant is orally used as an antipyretic and an anthelminthic, and topically employed as a treatment for joint pain. The juice from its leaves is traditionally used to treat conjunctivitis or inflammation.

*Dactyloctenium aegyptium* is a plant belonging to the family Poaceae, and is traditionally used as a decoction to treat fever. The whole plant can be crushed and steeped in alcohol to be used externally as an analgesic or an anti-inflammatory agent.

*Hopea ferrea* is a plant belonging to the family Dipterocarpaceae. The barks of this plant are used as tonic.

In the present invention, any given part of the above described plants, for example, a whole tree, a whole plant, leaves (including laminas and petioles), barks, xylems, wood, branches, fruits, pericarps, seeds, flowers (including petals and ovaries), roots, rhizomes, etc., or a combination thereof can be used. Preferred usable plant part include the wood of *Hiptage candicans*, the whole plant of *Piper sarmentosum*, the root of *Solanum stramonifolium*, the wood or bark of *Anaxagorea luzonensis*, the rhizome of *Smilax corbularia*, the root or stem of *Ardisia elliptica*, the leaves of *Erythrina suberosa*, the whole plant of *Dactyloctenium aegyptium*, and the bark of *Hopea ferrea*.

In the present invention, the above described plant may be directly used, or may also be used after it has been cut, crushed, ground or exploited. Otherwise, a dry product thereof may also be used. Preferably, a dry product of the plant is used. Also, such a dry product may be cut, crushed, ground or powdered.

The extract of the plant used in the present invention may be an extract obtained by directly extracting from each of the above described plants used in the present invention, or an extract obtained by extracting from each of the above described plants used in the present invention, which has been dried, cut, crushed, ground or exploited. Preferably, the extract of the plant used in the present invention is an extract from a dry product of the above described plants used in the present invention, or an extract from the dry product, which has been cut, crushed, ground or powdered.

Examples of an extraction means for obtaining the plant extract, which can be used herein, include ordinary extraction means, such as solid-liquid extraction, squeezing extraction, liquid-liquid extraction, immersion, decoction, percolation, reflux extraction, Soxhlet extraction, ultrasonic extraction, microwave extraction, and stirring. These extraction means may be used in combination. For example, immersion or solid-liquid extraction may be combined with liquid-liquid extraction. For reducing the extraction time, solid-liquid extraction involving stirring may be carried out.

The solvent used for extraction of the plant extract may be either a polar solvent or a nonpolar solvent, and these solvents may also be used in combination. Examples of the extraction solvent include: water; monohydric or polyhydric alcohols; ketones such as acetone or methyl ethyl ketone; esters such as methyl acetate or ethyl acetate; chain and cyclic ethers such as tetrahydrofuran or diethyl ether; polyethers such as polyethylene glycol; halogenated hydrocarbons such as dichloromethane, chloroform, or carbon tetrachloride; hydrocarbons such as hexane, cyclohexane, or petroleum ether; aromatic hydrocarbons such as benzene or toluene; pyridines; supercritical carbon dioxide; and fats and oils, waxes, and other oils. The above-listed solvents can be used singly or in combination of two or more solvents. An example of such a combination of solvents is a mixed solvent of monohydric alcohol or polyhydric alcohol and water.

Alternatively, the plant extract may also be prepared by repeated extraction using different solvents.

Examples of the monohydric alcohol include methanol, ethanol, propanol, butanol, amyl alcohol, hexanol, heptanol, and octanol. Examples of the polyhydric alcohol include: divalent alcohols such as ethylene glycol, propylene glycol, 1,3-butylene glycol, 1,4-butanediol, 1,5-pentanediol, or 1,6-hexanediol; and tri- or more hydric alcohols such as glycerin. Among these alcohols, monohydric or polyhydric alcohol having 1 to 4 carbon atoms is preferable, and from the viewpoint of versatility, monohydric alcohol and dihydric alcohol are preferable. More preferred examples include methanol, ethanol, 1,3-butylene glycol, n-propanol, isopropanol, n-butanol, isobutanol, sec-butanol, and t-butanol. Ethanol is further preferable.

Examples of a mixed solvent of monohydric alcohol or polyhydric alcohol and water include mixed solvents of the above-listed monohydric alcohols and water, and mixed solvents of the above-listed polyhydric alcohols and water. A preferred example is a mixed solvent of water and alcohol selected from the group consisting of methanol, ethanol, 1,3-butylene glycol, n-propanol, isopropanol, n-butanol, isobutanol, sec-butanol and t-butanol. A more preferred example is a mixed solvent of ethanol and water.

The concentration of alcohol in a mixed solvent of monohydric alcohol or polyhydric alcohol and water is, e.g. 10% by mass or more, preferably 20% by mass or more, more preferably 30% by mass or more, and even more preferably 50% by mass or more, and also, it is preferably 99.9% by mass or less, more preferably 99.5% by mass or less, and even more preferably 95% by mass or less. Otherwise, examples of the concentration of alcohol in the mixed solvent of water/alcohol include from 10 to 99.9% by mass, from 10 to 99.5% by mass, from 10 to 95% by mass, from 20 to 99.9% by mass, from 20 to 99.5% by mass, from 20 to 95% by mass, from 30 to 99.9% by mass, from 30 to 99.5% by mass, from 30 to 95% by mass, from 50 to 99.9% by mass, from 50 to 99.5% by mass, and from 50 to 95% by mass.

In a preferred embodiment, the solvent used in the extraction of a plant extract is selected from the group consisting of water, monohydric alcohol, polyhydric alcohol, a mixed solvent of monohydric alcohol or polyhydric alcohol and water, and hexane. The present solvent is more preferably water, ethanol, a mixed solvent of ethanol and water, or hexane.

Examples of the concentration of ethanol in the above described mixed solvent of ethanol and water include from 10 to 99.9 volume %, from 10 to 99.5 volume %, from 10 to 95 volume %, from 20 to 99.9 volume %, from 20 to 99.5 volume %, from 20 to 95 volume %, from 30 to 99.9 volume %, from 30 to 99.5 volume %, from 30 to 95 volume %, from 50 to 99.9 volume %, from 50 to 99.5 volume %, and from 50 to 95 volume %.

In a more preferred embodiment, the solvents used in the extraction of the plant used in the present invention are: water, 50% (v/v) ethanol aqueous solution or 95% (v/v) ethanol aqueous solution for *Hiptage candicans* and *Anaxagorea luzonensis*; 50% (v/v) ethanol aqueous solution, 95% (v/v) ethanol aqueous solution or hexane for *Piper sarmentosum, Smilax corbularia, Ardisia elliptica*, and *Erythrina suberosa*; hexane for *Solanum stramonifolium*; 95% (v/v) ethanol aqueous solution or hexane for *Dactyloctenium aegyptium*; and 50% (v/v) ethanol aqueous solution, 95% (v/v) ethanol aqueous solution or hexane for *Hopea ferrea*.

The amount of the solvent used in extraction is preferably from 1 to 100 mL with respect to 1 g of the plant (in terms of dry mass). Extraction conditions are not particularly limited, as long as extraction is sufficiently carried out under the conditions. In general, if the solvent is at a lower temperature, extraction is carried out for a longer period of time, and if the solvent is at a higher temperature, extraction is carried out for a shorter period of time. For example, the extraction time is preferably 1 hour or more, and more preferably 4 hours or more. On the other hand, it is preferably 2 months or less, and more preferably 4 weeks or less. Moreover, for example, the extraction temperature is preferably 0° C. or higher, and more preferably 5° C. or higher. Also, it is preferably a solvent boiling point or lower, and more preferably approximately 10° C. to 80° C., and it may also be approximately a room temperature. Examples of preferred extraction conditions include a temperature of from 15° C. to 40° C. for from 3 days to 4 weeks, and from 50° C. to 70° C. for from 1 to 10 hours. However, extraction conditions are not limited thereto, and can be selected, as appropriate, by a person skilled in the art.

A purification treatment, which is commonly used in the production of a plant extract, can be performed, as necessary, on the extract obtained by the aforementioned procedures. Examples of such a purification treatment include organic solvent precipitation, centrifugation, ultrafiltration membrane, high performance liquid chromatography, column chromatography, liquid-liquid distribution, gel filtration separation, and a treatment of using activated carbon or the like.

With regard to the extract obtained by the aforementioned procedures, the extract solution or a fraction thereof may be directly used singly or in combination, or it may be diluted with a suitable solvent and it may be then used in the form of a diluted solution. Otherwise, the extract may be processed into a concentrated extract, dry powder, or a paste, and it may be then used.

As will be described in Examples later, the plant used in the present invention or extract thereof has activity of inhibiting endothelin-converting enzyme (see Example 1). Accordingly, the plant used in the present invention or extract thereof can be used as an active ingredient for inhibiting endothelin-converting enzyme. Otherwise, the plant used in the present invention or extract thereof can be used as an active ingredient for suppression of endothelin activity, suppression of melanogenesis in skin melanocytes caused by an increase in the endothelin activity, skin whitening, or prevention or amelioration of symptoms or conditions caused by an increase in the endothelin activity.

According to the present invention, at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof can be used as an active ingredient. The plants used in the present invention and extracts thereof may be used singly, or may also be used in combination of any two or more. In a preferred embodiment, an extract from *Hiptage candicans, Piper sarmentosum, Solanum stramonifolium, Anaxagorea luzonensis, Smilax corbularia, Ardisia elliptica, Erythrina suberosa, Dactyloctenium aegyptium* or *Hopea ferrea*, or a combination of two or more selected from the group consisting of the extracts is used.

Accordingly, in one aspect, the present invention provides an endothelin-converting enzyme inhibitor comprising, as an active ingredient, at least one selected from the group consisting of the plants used in the present invention and extracts thereof. In addition, the present invention provides a melanogenesis inhibitor comprising, as an active ingredient, at least one selected from the group consisting of the plants used in the present invention and extracts thereof. Moreover, the present invention provides a skin whitening agent comprising, as an active ingredient, at least one selected from the group consisting of the plants used in the present invention and extracts thereof. Furthermore, the present invention provides an antihypertensive agent comprising, as an active ingredient, at least one selected from the group consisting of the plants used in the present invention and extracts thereof.

In another aspect, the present invention provides use of at least one selected from the group consisting of the plants used in the present invention and extracts thereof, for producing an endothelin-converting enzyme inhibitor, a melanogenesis inhibitor, a skin whitening agent, or an antihypertensive agent.

In one embodiment, the above described agent can be essentially composed of at least one selected from the group consisting of the plants used in the present invention and extracts thereof.

In another aspect, the present invention provides use of at least one selected from the group consisting of the plants used in the present invention and extracts thereof, for inhibiting endothelin-converting enzyme, inhibiting melanogenesis, whitening skin, or preventing or ameliorating hypertension.

In still another aspect, the present invention provides at least one selected from the group consisting of the plants used in the present invention and extracts thereof, for use in inhibiting endothelin-converting enzyme, inhibiting melanogenesis, whitening skin, or preventing or ameliorating hypertension.

The above described use according to the present invention may be either therapeutic use or non-therapeutic use. Examples of the therapeutic use include use for a patient affected with hypertension, and use for a patient affected with a disease caused by overproduction of melanin (e.g., chloasma, acquired dermal melanocytosis, etc.). Examples of the non-therapeutic use include use for prevention of an increase in the blood pressure of a person who has a relatively high blood pressure but has not yet been diagnosed as having hypertension, and use for inhibition of skin melanogenesis or skin whitening for cosmetic purposes. Moreover, another example of the non-therapeutic use is the provision of the plants used in the present invention or extracts thereof to another person by the administration or inception thereof, not as a medical treatment, but for obtaining the effect of preventing an increase in blood pressure, or the effect of inhibiting skin melanogenesis or whitening skin.

The plants used in the present invention and extracts thereof can be used for both a human and a non-human animal. Examples of such a non-human animal include non-human mammals and birds. Examples of such a non-human mammal include an anthropoid (ape), other primates, a mouse, a rat, a hamster, a horse, a bovine, a swine, a sheep, a goat, a dog, a cat, and a companion animal.

The plants used in the present invention and extracts thereof can be added to pharmaceutical products, quasi drugs, cosmetics, food products and the like, as an active ingredient for imparting a function such as endothelin-converting enzyme inhibition, melanogenesis inhibition, skin whitening, or prevention or amelioration of hypertension. For example, the plants used in the present invention and extracts thereof are comprised in a composition for inhibiting endothelin-converting enzyme, inhibiting melanogenesis, whitening skin, or preventing or ameliorating hypertension. This composition is preferably a pharmaceutical product, a quasi drug, a cosmetic, or a food composition.

The above described pharmaceutical product (including quasi drug) is for use in endothelin-converting enzyme inhibition, melanogenesis inhibition, or prevention or amelioration of hypertension, and comprises at least one selected from the group consisting of the plants used in the present invention and extracts thereof as an active ingredient for exhibiting the aforementioned function. Furthermore, the pharmaceutical product may also comprise pharmaceutically acceptable carriers, other active ingredients, pharmacological components, and the like, as necessary, unless the function of the active ingredient is lost.

The administration form of the above described pharmaceutical product (including quasi drug) may be either oral administration or parenteral administration. The dosage form of the pharmaceutical product is not particularly limited, as long as it is a dosage form suitable for oral or parenteral administration. Examples of such a dosage form include an injection, a suppository, an inhalant, a transdermal absorption agent, various types of external agents, a topical formulation, a tablet, a capsule, a granule, a powder agent, a liquid agent, and syrup. These formulations having various dosage forms can be prepared by appropriately combining at least one selected from the group consisting of the plants used in the present invention and extracts thereof with a pharmaceutically acceptable carrier (e.g., an excipient, a binder, a filler, a thickener, a disintegrator, a surfactant, a lubricant, a dispersant, a buffer, a preservative, a corrigent, a flavor, a coating agent, a diluent, etc.), other medicinal components and the like according to an ordinary method.

The content (in terms of dry mass) of the plants used in the present invention or extracts thereof in the above described pharmaceutical product (including quasi drug) is not particularly limited. It is preferably 0.01% by mass or more, more preferably 0.1% by mass or more, even more preferably 1.0% by mass or more, further preferably 10% by mass or more, and even further preferably 15% by mass or more, based on the total mass, and it is preferably 95% by mass or less, more preferably 80% by mass or less, and even more preferably 60% by mass or less, based on the total mass. Moreover, examples of the content include from 0.01 to 95% by mass, from 0.01 to 80% by mass, from 0.01 to 60% by mass, from 0.1 to 95% by mass, from 0.1 to 80% by mass %, from 0.1 to 60% by mass, from 1.0 to 95% by mass, from 1.0 to 80% by mass, from 1.0 to 60% by mass, from 10 to 95% by mass, from 10 to 80% by mass, from 10 to 60% by mass, from 15 to 95% by mass, from 15 to 80% by mass, and from 15 to 60% by mass.

The above described cosmetic is for use in endothelin-converting enzyme inhibition, melanogenesis inhibition or skin whitening, and comprises at least one selected from the group consisting of the plants used in the present invention and extracts thereof as an active ingredient for exhibiting the aforementioned function. Furthermore, the cosmetic may also comprise a carrier acceptable for cosmetics, or other active ingredients or cosmetic components, such as a moisturizer, other whitening agents, a UV protectant, a cell activator, a cleaning agent, a keratolytic agent, a makeup component (e.g., makeup base, foundation, face powder, powder, cheek color, lipstick, eye makeup, eyebrow, mascara, and others), and the like, as necessary, unless the function of the active ingredient is lost. Examples of the form of the cosmetic include cosmetic forms for external administration to the skin, local administration, and oral administration.

The above described cosmetic can be produced by combining at least one selected from the group consisting of the plants used in the present invention and extracts thereof with the above described carrier acceptable for cosmetics, or other active ingredients or cosmetic components, and the like, as necessary, according to an ordinary method.

The content of the plants used in the present invention or extracts thereof (in terms of dry mass) in the above described cosmetic is not particularly limited. It is preferably 0.0001% by mass or more, more preferably 0.001% by mass or more, even more preferably 0.01% by mass or more, further preferably 0.1% by mass or more, and even further preferably 1.0% by mass or more, based on the total mass and, it is preferably 60% by mass or less, more preferably 40% by mass or less, even more preferably 20% by mass or less, and even further preferably 10% by mass or less, based on the total mass. Moreover, examples of the content include from 0.0001 to 60% by mass, from 0.0001 to 40% by mass, from 0.0001 to 20% by mass, from 0.0001 to 10% by mass, from 0.001 to 60% by mass, from 0.001 to 40% by mass, from 0.001 to 20% by mass, from 0.001 to 10% by mass, from 0.01 to 60% by mass, from 0.01 to 40% by mass, from 0.01 to 20% by mass, from 0.01 to 10% by mass, from 0.1 to 60% by mass, from 0.1 to 40% by mass, from 0.1 to 20% by mass, from 0.1 to 10% by mass, from 1.0 to 60% by mass, from 1.0 to 40% by mass, from 1.0 to 20% by mass, and from 1.0 to 10% by mass.

The above described food product is for use in providing a function such as endothelin-converting enzyme inhibition, melanogenesis inhibition, skin whitening, or prevention or amelioration of hypertension, and comprises at least one selected from the group consisting of the plants used in the present invention and extracts thereof as an active ingredient for exhibiting the aforementioned function. The food product includes food products for sick persons and food products with health claims, such as food products with nutrient function claims, food products for specified health uses, or food products with a labeling system on food functions, the concept of each of which is endothelin-converting enzyme inhibition, melanogenesis inhibition, skin whitening, or prevention or amelioration of hypertension and which are attended with a labeling system on the concept, as necessary.

The above described food product may be a solid, semi-solid, or liquid (e.g., beverages) food composition. Examples of the food composition include breads, needles, rice products, confectioneries such as cookies, jellies, dairy products, soup products, frozen food products, convenience food products, processed starch products, processed fish meat products, other processed food products, condiments, supplements, beverages such as tea or coffee beverages, fruit drinks, carbonated drinks or jelly-like drinks, and the raw materials thereof. Alternatively, the food product may also be a supplement having the form of an oral administration preparation, such as a tablet, a capsule, a granule, powder, a liquid agent, or syrup.

The above described food product can be produced as a food composition by appropriately combining at least one selected from the group consisting of the plants used in the present invention and extracts thereof with any given food product materials or additives acceptably used for food products (e.g., a solvent, a softener, oil, an emulsifier, an antiseptic, a flavor, a sweetener, a stabilizer, a coloring agent, an ultraviolet absorber, an antioxidant, a moisturizer, a thickener, a fixing agent, a dispersant, a wetting agent, etc.) according to an ordinary method.

The content of the plants used in the present invention or extracts thereof (in terms of dry mass) in the above described food composition is not particularly limited. It is preferably 0.0001% by mass or more, more preferably 0.001% by mass or more, even more preferably 0.01% by mass or more, further preferably 0.1% by mass or more, and even further preferably 1.0% by mass or more, based on the total mass and, it is preferably 60% by mass or less, more preferably 40% by mass or less, even more preferably 20% by mass or less, and even further preferably 10% by mass or less, based on the total mass. Moreover, examples of the content include from 0.0001 to 60% by mass, from 0.0001 to 40% by mass, from 0.0001 to 20% by mass, from 0.0001 to 10% by mass, from 0.001 to 60% by mass, from 0.001 to 40% by mass, from 0.001 to 20% by mass, from 0.001 to 10% by mass, from 0.01 to 60% by mass, from 0.01 to 40% by mass, from 0.01 to 20% by mass, from 0.01 to 10% by mass, from 0.1 to 60% by mass, from 0.1 to 40% by mass, from 0.1 to 20% by mass, from 0.1 to 10% by mass, from 1.0 to 60% by mass, from 1.0 to 40% by mass, from 1.0 to 20% by mass, and from 1.0 to 10% by mass.

In another embodiment, the present invention provides a method of inhibiting endothelin-converting enzyme in a subject. In addition, the present invention provides a method of inhibiting melanogenesis in a subject. Moreover, the present invention provides a method of whitening skin in a subject. Furthermore, the present invention provides a method of preventing or ameliorating hypertension in a subject. These methods comprise administering to a subject an effective amount of at least one selected from the group consisting of the plants used in the present invention and extracts thereof. These methods may be either therapeutic methods or non-therapeutic methods.

The subject in the above described methods is an animal, for which endothelin-converting enzyme inhibition, melanogenesis inhibition, skin whitening or prevention or amelioration of hypertension is desired, or which needs it. Examples of such an animal include the aforementioned human and non-human animals, and the animal is more preferably a human. Otherwise, examples of the subject in the above described methods include sites on the skin, for which whitening is desired, or which need it (e.g., sites on the skin having pigmentation, spots, senile pigment freckle, etc. and light-exposure sites on the skin).

The present invention further provides a method of inhibiting in vitro endothelin-converting enzyme or melanogenesis. This in vitro method can be carried out on the aforementioned human or non-human animal-derived tissues or cells, for example, vascular endothelial cells, vascular tissues, or skin cells such as skin tissues, 3D cultured skin or cultured keratinocytes, or an extract solution thereof, or a reaction solution comprising endothelin-converting enzyme and Big ET-1, Big ET-2 or Big ET-3 as a substrate thereof.

The effective dose amount to be administered in the above described methods of the present invention can be an amount, in which endothelin-converting enzyme activity in a subject can be inhibited. The effective amount is preferably an amount, in which the activity of endothelin-converting enzyme in an administration group can be statistically significantly reduced in compared to that in a non-administration group. Also, the effective amount is preferably an amount, in which the activity of endothelin-converting enzyme in an administration group can be reduced to 40% or less, more preferably 30% or less, and even more preferably 15% or less of that in a non-administration group. The activity of endothelin-converting enzyme can be measured by the methods described in the after-mentioned Examples or Non-Patent Document 4.

The applied dose of the plants used in the present invention or extracts thereof and the administration plan may be appropriately determined by a person skilled in the art depending on the species, body weight, sex, age or condition of a subject, or other factors. The applied dose of the plants used in the present invention or extracts thereof (in terms of dry product weight) per adult per day is preferably 0.0001 mg or more, more preferably 0.001 mg or more, even more preferably 0.01 mg or more, further preferably 0.1 mg or more, even further preferably 1 mg or more, and still further preferably 0.1 g or more, and it is also preferably 10 g or less, more preferably 5 g or less, and even more preferably 1 g or less, but the dose is not limited thereto. Otherwise, the applied dose (per adult per day) of the plants used in the present invention or extracts thereof (in terms of dry product weight) can be selected from the range of from 0.0001 mg to 10 g, from 0.0001 mg to 5 g, from 0.0001 mg to 1 g, from 0.001 mg to 10 g, from 0.001 mg to 5 g, from 0.001 mg to 1 g, from 0.01 mg to 10 g, from 0.01 mg to 5 g, from 0.01 mg to 1 g, from 0.1 mg to 10 g, from 0.1 mg to 5 g, from 0.1 mg to 1 g, from 1 mg to 10 g, from 1 mg to 5 g, from 1 mg to 1 g, from 0.1 g to 10 g, from 0.1 g to 5 g, or from 0.1 g to 1 g. It is preferable to divide the above described amount, for example, once a day, or two or three times a day, and to continuously administer it to a subject for several weeks to several months.

Also, the present invention includes, as illustrative embodiments, the following substances, production methods, intended uses, methods, and the like. However, the present invention is not limited to these embodiments.

[1] An endothelin-converting enzyme inhibitor, comprising, as an active ingredient, at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[2] A melanogenesis inhibitor, comprising, as an active ingredient, at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[3] A skin whitening agent, comprising, as an active ingredient, at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[4] An antihypertensive agent, comprising, as an active ingredient, at least one selected from the group consisting of *Hiptage candicans, Solanum stramonifolium, Anaxagorea luzonensis, Smilax corbularia, Ardisia elliptica, Erythrina suberosa, Dactyloctenium aegyptium, Hopea ferrea* and extracts thereof.

[5] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for production of an endothelin-converting enzyme inhibitor.

[6] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for production of a melanogenesis inhibitor.

[7] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for production of a skin whitening agent.

[8] Use of at least one selected from the group consisting of *Hiptage candicans, Solanum stramonifolium, Anaxagorea luzonensis, Smilax corbularia, Ardisia elliptica, Erythrina suberosa, Dactyloctenium aegyptium, Hopea ferrea* and extracts thereof, for production of an antihypertensive agent.

[9] At least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for use in inhibiting endothelin-converting enzyme.

[10] At least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for use in inhibiting melanogenesis.

[11] At least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for use in skin whitening.

[12] At least one selected from the group consisting of *Hiptage candicans, Solanum stramonifolium, Anaxagorea luzonensis, Smilax corbularia, Ardisia elliptica, Erythrina suberosa, Dactyloctenium aegyptium, Hopea ferrea* and extracts thereof, for use in preventing or ameliorating hypertension.

[13] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for inhibiting endothelin-converting enzyme.

[14] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for inhibiting melanogenesis.

[15] Use of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof, for whitening skin.

[16] Use of at least one selected from the group consisting of *Hiptage candicans, Solanum stramonifolium, Anaxagorea luzonensis, Smilax corbularia, Ardisia elliptica, Erythrina suberosa, Dactyloctenium aegyptium, Hopea ferrea* and extracts thereof, for preventing or ameliorating hypertension.

[17] A method of inhibiting endothelin-converting enzyme in a subject, comprising administrating to the subject in need thereof an effective amount of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[18] A method of inhibiting melanogenesis in a subject, comprising administrating to the subject in need thereof an effective amount of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[19] A method of whitening skin in a subject, comprising administrating to the subject in need thereof an effective amount of at least one selected from the group consisting of *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof.

[20] A method of preventing or ameliorating hypertension in a subject, comprising administrating to the subject in need thereof an effective amount of at least one selected from the group consisting of *Hiptage candicans, Solanum stramonifolium, Anaxagorea luzonensis, Smilax corbularia, Ardisia elliptica, Erythrina suberosa, Dactyloctenium aegyptium, Hopea ferrea* and extracts thereof.

[21] A composition of an endothelin-converting enzyme inhibitor, comprising, as an active ingredient, at least one extract selected from the group consisting of extracts of *Hiptage candicans, Piper sarmentosum, Solanum stramonifolium, Anaxagorea luzonensis, Smilax corbularia, Ardisia elliptica, Erythrina suberosa, Dactyloctenium aegyptium,* and *Hopea ferrea* in cosmetic components, and comprising a pharmaceutically acceptable carrier or a food additive.

[22] The composition according to claim 21, wherein the content of the extract is,
preferably from 0.0001 to 60% by mass,
more preferably from 0.0001 to 40% by mass,
even more preferably from 0.0001 to 20% by mass,
even more preferably from 0.0001 to 10% by mass,
even more preferably from 0.001 to 60% by mass,
even more preferably from 0.001 to 40% by mass,
even more preferably from 0.001 to 20% by mass,
even more preferably from 0.001 to 10% by mass,
even more preferably from 0.01 to 60% by mass,
even more preferably from 0.01 to 40% by mass,
even more preferably from 0.01 to 20% by mass,
even more preferably from 0.01 to 10% by mass.

[23] The composition according to claim 21 or 22, wherein the cosmetic components comprise one or more selected from the group consisting of a moisturizer, a whitening agent, a UV protectant, a cell activator, a cleaning agent, a keratolytic agent, a makeup component, and a carrier acceptable for cosmetics.

[24] The composition according to any one of claims 21 to 23, wherein the pharmaceutically acceptable carrier is one or more selected from the group consisting of an excipient, a binder, a filler, a thickener, a disintegrator, a surfactant, a lubricant, a dispersant, a buffer, a preservative, a corrigent, a flavor, a coating agent, and a diluent.

[25] The composition according to any one of claims 21 to 24, wherein the food additive is one or more selected from the group consisting of a solvent, a softener, oil, an emulsifier, an antiseptic, a flavor, a sweetener, a stabilizer, a coloring agent, an ultraviolet absorber, an antioxidant, a moisturizer, a thickener, a fixing agent, a dispersant, and a wetting agent.

[26] In any one of the above [1], [5], [9], [13] [17] and [21]-[25], the endothelin-converting enzyme is preferably endothelin-converting enzyme 1.

[27] In any one of the above [13] to [16], the use is preferably non-therapeutic use.

[28] In any one of the above [1] to [27], the extract is preferably an extract obtained using water, ethanol, a mixed solvent of ethanol and water, or hexane.

[29] In the above [28], the extract is preferably,
an extract from *Hiptage candicans*, which is obtained using water, 50% (v/v) ethanol aqueous solution or 95% (v/v) ethanol aqueous solution,
an extract from *Piper sarmentosum*, which is obtained using 50% (v/v) ethanol aqueous solution, 95% (v/v) ethanol aqueous solution or hexane,
an extract from *Solanum stramonifolium* obtained using hexane,
an extract from *Anaxagorea luzonensis*, which is obtained using water, 50% (v/v) ethanol aqueous solution or 95% (v/v) ethanol aqueous solution,
an extract from *Smilax corbularia*, which is obtained using 50% (v/v) ethanol aqueous solution, 95% (v/v) ethanol aqueous solution or hexane,
an extract from *Ardisia elliptica*, which is obtained using 50% (v/v) ethanol aqueous solution, 95% (v/v) ethanol aqueous solution or hexane,
an extract from *Erythrina suberosa*, which is obtained using 50% (v/v) ethanol aqueous solution, 95% (v/v) ethanol aqueous solution or hexane,
an extract from *Dactyloctenium aegyptium*, which is obtained using 95% (v/v) ethanol aqueous solution or hexane, or
an extract from *Hopea ferrea*, which is obtained using 50% (v/v) ethanol aqueous solution, 95% (v/v) ethanol aqueous solution or hexane.

[30] In any one of the above [1] to [29], preferably,
the *Hiptage candicans* is the wood of *Hiptage candicans*,
the *Piper sarmentosum* is the whole plant of *Piper sarmentosum*,
the *Solanum stramonifolium* is the root of *Solanum stramonifolium*,
the *Anaxagorea luzonensis* is the wood or bark of *Anaxagorea luzonensis*,
the *Smilax corbularia* is the rhizome of *Smilax corbularia*,
the *Ardisia elliptica* is the root or stem of *Ardisia elliptica*,
the *Erythrina suberosa* is the leaves of *Erythrina suberosa*,
the *Dactyloctenium aegyptium* is the whole plant of *Dactyloctenium aegyptium*, and
the *Hopea ferrea* is the bark of *Hopea ferrea*.

EXAMPLES (Preparation of Plant Extracts)

Dried and crushed plant materials were each extracted with any of the following four types of solvent: (A) water, (B) 50% (v/v) ethanol aqueous solution, (C) 95% (v/v) ethanol aqueous solution, and (D) hexane. Approximately 50 g of each plant material was immersed in 500 mL of water at 60° C. for 4 hours, or in 500 mL of 50% (v/v) ethanol aqueous solution, 95% (v/v) ethanol aqueous solution, ethanol or hexane at 30° C. for 7 days. Thereafter, the resultants were filtrated to obtain crude extract solutions, and the crude extract solutions were then concentrated to dryness to obtain various extract solids. The extract solids were each dissolved in various types of solvents (A: 10% EtOH, B: 50% EtOH, C: 95% EtOH, and D: 99.5% EtOH), so that the solid concentrations became 1% (w/v), 0.5% (w/v), and 0.25% (w/v). The plant extract solutions were each preserved at −20° C., until they were used in the after-mentioned ECE inhibitory assay. The yields of the extract solids are shown in Table 1.

TABLE 1

| | | Yield of extract (dry weight, g) | | | |
|---|---|---|---|---|---|
| Plant species | | Water Extract | 50% EtOH Extract | 95% EtOH Extract | Hexane Extract |
| *Hiptage candicans* | Wood | 1.04 | 5.03 | 4.39 | — |
| *Piper sarmentosum* | Whole plant | — | 5.02 | 3.80 | 0.40 |

TABLE 1-continued

| | | Yield of extract (dry weight, g) | | | |
|---|---|---|---|---|---|
| Plant species | | Water Extract | 50% EtOH Extract | 95% EtOH Extract | Hexane Extract |
| *Solanum stramonifolium* | Root | — | — | — | 0.08 |
| *Anaxagorea luzonensis* | Wood or bark | 3.80 | 7.46 | 8.16 | — |
| *Smilax corbularia* | Rhizome | — | 10.36 | 9.52 | 0.08 |
| *Ardisia elliptica* | Root or stem | — | 1.96 | 2.00 | 0.55 |
| *Erythrina suberosa* | Leaves | — | 5.08 | 2.50 | 1.22 |
| *Dactyloctenium aegyptium* | Whole plant | — | — | 5.02 | 0.48 |
| *Hopea ferrea* | Bark | — | 4.30 | 3.79 | 0.19 |

(Crude Endothelin-Converting Enzyme Protein)

In accordance with the method described in Non-Patent Document 4, a crude ECE-1 protein was newly prepared by extracting it from a fresh human vascular endothelial cell line EA.hy926. The crude ECE-1 protein was preserved at −18° C., until it was used.

Example 1

ECE Inhibitory Assay

An enzyme reaction was carried out by the procedures described in Non-Patent Document 4. Briefly speaking, an each plant extract (final concentration: 0.01, 0.005, or 0.0025% (w/v)) and a crude ECE-1 protein were pre-incubated in a BigET-1 buffer (0.1 M sodium phosphate buffer (pH 6.8), 0.5 M NaCl) at 37° C. for 15 minutes. Thereafter, a 0.2 µM BigET-1 substrate (Enzo Life Sciences, Cat. #ALX-152-001-PC05) in a BigET-1 buffer (final concentration: 0.1 µM) was added to the reaction solution, and the obtained mixture was then incubated at 37° Cr for 2 hours. After 5 mM EDTA had been added to the reaction solution to terminate the enzyme reaction, the mixed solution was transferred to ET-1 ELISA kit (Enzo Life Sciences, Cat. #ADI-900-020A), and ET-1 was then quantified according to the method described in the production manual. Briefly speaking, ET-1 in the mixed solution was captured by an anti-human ET-1 antibody immobilized on a 96-well microplate and was then labeled with a HRP-labeled anti-human ET-1 antibody. The absorbance of the labeled ET-1 at 450 nm was measured using a plate reader. The amount of ET-1 in the mixed solution was quantified based on a comparison made with the absorbance of a standard, and then, relative ECE-1 inhibitory activity (% relative to a control) was calculated according to the following formula.

Relative ECE-1 inhibitory activity (%)=(1−X/Y)*100

(X; the amount of ET-1 in a liquid containing a plant extract, Y; the amount of ET-1 in a liquid containing a control)

Phosphoramidon (PD) was used as a positive control of the ECE-1 inhibitor. 10% (v/v) ethanol aqueous solution, 50% (v/v) ethanol aqueous solution, 95% (v/v) ethanol aqueous solution or 100% ethanol was used as a control.

The results obtained by quantifying ECE-1 inhibitory activity are shown in Table 2. All of the extracts from *Hiptage candicans, Piper sarmentosum, Solanum stramonifolium, Anaxagorea luzonensis, Smilax corbularia, Ardisia elliptica, Erythrina suberosa, Dactyloctenium aegyptium* and *Hopea ferrea* had ECE-1 inhibitory activity. The activities of these plant extracts were higher than the activity of burnet (*Sanguisorba officinalis* L.) extract (Reference Example 1) which is a known ECE-1 inhibitor described in Non-Patent Document 4. As described in Non-Patent Document 4, the burnet extract as an ECE-1 inhibitor suppresses skin pigmentation. In addition, Non-Patent Document 4 describes that a plant extract which inhibits ET-1 suppresses the growth of melanocytes and prevents human skin pigmentation after UVB irradiation. Therefore, *Hiptage candicans, Piper sarmentosum, Solanum stramonifolium, Anaxagorea luzonensis, Smilax corbularia, Ardisia elliptica, Erythrina suberosa, Dactyloctenium aegyptium, Hopea ferrea* and extracts thereof are also suggested to have activity of inhibiting melanogenesis on skin and preventing pigmentation. Moreover, the above described plants and extracts thereof suppress vasoconstriction based on the ECE inhibitory activity and are effective as antihypertensive agents.

TABLE 2

| | | Relative ECE-1 inhibitory activity (%) | | |
|---|---|---|---|---|
| Plant species | extraction solvent | 0.01% (w/v) Extract | 0.005% (w/v) Extract | 0.0025% (w/v) Extract |
| *Hiptage candicans* | Water | 79.4 | — | — |
| | 50% EtOH | 91.3 | 90.8 | 88.7 |
| | 95% EtOH | 90.3 | 90.8 | 88.9 |
| *Piper sarmentosum* | 50% EtOH | 87.0 | 72.2 | 67.0 |
| | 95% EtOH | 91.7 | 89.1 | 85.3 |
| | Hexane | 88.2 | 87.5 | 82.0 |
| *Solanum stramonifolium* | Hexane | 87.6 | 86.5 | 80.8 |
| *Anaxagorea luzonensis* | Water | 85.7 | — | — |
| | 50% EtOH | 90.1 | 91.7 | 89.6 |
| | 95% EtOH | 90.5 | 90.9 | 85.9 |
| *Smilax corbularia* | 50% EtOH | 87.2 | — | — |
| | 95% EtOH | 88.2 | — | — |
| | Hexane | 88.0 | 87.5 | 86.1 |
| *Ardisia elliptica* | 50% EtOH | 89.7 | — | — |
| | 95% EtOH | 93.3 | 90.9 | 80.5 |
| | Hexane | 92.4 | 89.1 | 89.4 |
| *Erythrina suberosa* | 50% EtOH | 80.3 | — | — |
| | 95% EtOH | 90.1 | 84.7 | 82.0 |
| | Hexane | 85.7 | — | — |
| *Dactyloctenium aegyptium* | 95% EtOH | 88.5 | 82.6 | 70.4 |
| | Hexane | 88.2 | 88.1 | 87.7 |

TABLE 2-continued

| Plant species | extraction solvent | Relative ECE-1 inhibitory activity (%) | | |
|---|---|---|---|---|
| | | 0.01% (w/v) Extract | 0.005% (w/v) Extract | 0.0025% (w/v) Extract |
| *Hopea ferrea* | 50% EtOH | 71.89 | 33.86 | 17.03 |
| | 95% EtOH | 84.87 | 82.40 | 77.05 |
| | Hexane | 71.92 | 52.02 | 14.05 |
| Reference Example 1 Extract of *Sanguisorba officinalis* L. (purchased from Maruzen Pharmaceutical Co. Ltd.) | | 80.3 | — | — |

The invention claimed is:

1. A method of whitening skin in a subject in need thereof, comprising administering to the subject in need thereof an effective amount of *Hiptage candicans* or an extract thereof.

2. A method of delaying the onset of symptoms of hypertension in a subject in need thereof, comprising administering to the subject in need thereof an effective amount of *Hiptage candicans* or an extract thereof.

3. The method of claim 1, wherein *Hiptage candicans* is administered.

4. The method of claim 2, wherein *Hiptage candicans* is administered.

5. The method of claim 1, wherein an extract of *Hiptage candicans* is administered.

6. The method of claim 2, wherein an extract of *Hiptage candicans* is administered.

* * * * *